(12) United States Patent
Husain

(10) Patent No.: US 11,293,846 B2
(45) Date of Patent: Apr. 5, 2022

(54) DEVICE FOR TEST MILLING AN ORE SAMPLE

(71) Applicant: SGS NORTH AMERICA INC., Rutherford, NJ (US)

(72) Inventor: Khiratt Husain, Markham (CA)

(73) Assignee: SGS North America Inc., Rutherford, NJ (US)

(*) Notice: Subject to any disclaimer, the term of this patent is extended or adjusted under 35 U.S.C. 154(b) by 0 days.

(21) Appl. No.: 16/832,919

(22) Filed: Mar. 27, 2020

(65) Prior Publication Data

US 2020/0309655 A1    Oct. 1, 2020

Related U.S. Application Data

(60) Provisional application No. 62/824,378, filed on Mar. 27, 2019.

(51) Int. Cl.
*G01N 3/56* (2006.01)
*G01N 33/24* (2006.01)

(52) U.S. Cl.
CPC .............. *G01N 3/565* (2013.01); *G01N 33/24* (2013.01)

(58) Field of Classification Search
CPC ............................... G01N 3/565; G01N 33/24
USPC .............. 241/24.1–25, 68–81, 83–95, 46.15, 241/103–106, 170–184; 73/7
See application file for complete search history.

(56) References Cited

U.S. PATENT DOCUMENTS

| | | | |
|---|---|---|---|
| 3,253,744 A | 5/1966 | Macpherson et al. | |
| 3,716,196 A | 2/1973 | Motek et al. | |
| 3,810,002 A * | 5/1974 | Sata | B24B 49/00 324/236 |
| 4,459,783 A * | 7/1984 | Odell, II | B24B 49/00 177/245 |
| 4,874,947 A * | 10/1989 | Ward | H01J 37/3005 850/1 |
| 5,218,013 A * | 6/1993 | Schock | B29C 67/243 523/209 |
| 5,954,276 A | 9/1999 | Hintikka et al. | |
| 2009/0199625 A1 | 8/2009 | Kojovic et al. | |
| 2013/0119172 A1* | 5/2013 | Virdis | B02C 4/42 241/27 |
| 2013/0248626 A1* | 9/2013 | Held | B02C 25/00 241/30 |
| 2019/0119047 A1* | 4/2019 | Marsolek | F16H 55/36 |

OTHER PUBLICATIONS

Authorized Officer Joelle Vicenzi, International Search Report and Written Opinion for related international application PCT/US2020/025385, dated Jun. 15, 2020, 13 pages.

* cited by examiner

*Primary Examiner* — Robert R Raevis

(74) *Attorney, Agent, or Firm* — Fish & Richardson P.C.

(57) ABSTRACT

A device for generating milling measurement data at an output includes a support structure. A measurement station is supported by the support structure for measuring an attribute of milled material collected thereon and outputting a measurement of the attribute to the output. A mill is supported by the support structure above the measurement station for, while engaged, performing a continuous milling action on a feed material, and continuously or regularly depositing milled material onto the measurement station wherein the measurement station can measure the milled material without interrupting the milling action.

25 Claims, 15 Drawing Sheets

DEVICE FOR TEST MILLING AN ORE SAMPLE

REFERENCE TO APPLICATION

The present disclosure claims priority benefit from U.S. Provisional application 62/824,378, filed Mar. 27, 2019, entitled DEVICE FOR TEST MILLING AN ORE SAMPLE, and the entire disclosure set forth therein is incorporated herein by reference.

FIELD OF THE DISCLOSURE

The present disclosure relates to SPI testing procedures.

BACKGROUND

The Standard SAG (Semi-Autogenous Grinding) Power Index (SPI) procedure involves milling a prepared feed sample in the SPI mill for a set time, removing, screening, weighing an oversized fraction and returning the entire sample to the mill in several iterations (hereinafter referred to as "reset iterations.")

The Standard SAG Power Index (SPI) Test, developed in 1991, is now a Standard Metallurgical Test in the mining industry. It is used to estimate the hardness variability of an ore body, in grinding circuit design, optimization and production forecasting.

The SPI time is used to estimate the SAG specific energy of a feed sample or block using the relationship, under formula:

$$kWh/t = K[SPI/\sqrt{(T_{80})}]^n A \quad \text{(Equation 1)}$$

where:

K and n are constants, $T_{80}$ is the transfer size of the SAG product;

A is a correction factor for the feed size, pebble crushing and circulating load; and SPI is SAG Power Index value measured in minutes.

The SPI Test is performed in a laboratory scale SPI mill with a prepared feed sample weighing 2 kg and in a condition in which 80% of the feed sample passes through a ½ inch (12.7 mm) mesh screen. The objective of the Standard SPI Test is to estimate the time it takes to grind the feed sample to a target condition in which 80% of the feed sample passes through a 1.7 mm mesh screen. The feed sample is milled for a successive number of repeated set time intervals. After each time interval, the SPI mill must be shut down, and the sample entirely removed, screened, weighed and then the entire sample must be returned to the SPI mill to repeat the milling step for the next time interval. This is repeated until the target condition is reached. This procedure, especially on competent (hard) ores, is time consuming, is labour intensive, results in a limited number of data points, and introduces a number of sources of error in the management of the feed sample arising from the handling of the feed sample and the SPI mill throughout the SPI test. For instance, there is a risk that not all sample material is removed from the SPI mill, leading to varying amounts of unscreened residue remaining in the processing chamber at each reset iteration, or an error in not (or incorrectly) resetting for the next iteration.

SUMMARY

In an aspect, there is provided a device for generating milling measurement data at an output, comprising a support structure. A measurement station may be supported by the support structure for measuring an attribute of milled material collected thereon and outputting a measurement of the attribute to the output. A mill may be supported by the support structure above the measurement station for, while engaged, performing a milling action on a feed material, and depositing milled material onto the measurement station wherein the measurement station can measure the milled material without interrupting the milling action.

In some example embodiments, the mill may be configured to continuously, regularly, irregularly or intermittently perform the milling action.

In some example embodiments, the mill may be configured to continuously, regularly, irregularly or intermittently deposit milled material onto the measurement station.

In some example embodiments, the measurement station may be configured to continuously regularly, irregularly or intermittently measure the attribute, and wherein the attribute may be a weight of the milled material collected on the measurement station. Other attributes may also be monitored in addition to or in place of a weight attribute, depending on a desired test.

In some example embodiments, the measurement station may comprise a weighing structure to weigh the milled material collected thereon.

In some example embodiments, the measurement station may be configured to continuously regularly, irregularly or intermittently output a measurement of the attribute.

In some example embodiments, the output may be selected from at least one of a display, a scale or an input to a computer system.

In some example embodiments, the mill may comprise a processing chamber for holding the feed material while it performs the milling action thereon.

In some example embodiments, the processing chamber may comprise a plurality of test milling balls.

In some example embodiments, the processing chamber may comprise an inlet aperture for accepting the feed material.

In some example embodiments, the processing chamber may comprise an outlet aperture for depositing the milled material onto the measurement station, In some example embodiments, the input aperture and the outlet aperture may be the same.

Some example embodiments may further comprise a mesh cover to cover the outlet aperture, which may have openings of an opening size therein to deposit the milled material that is of a size less than the opening size onto the measurement station.

In some example embodiments, the mesh cover may be removable.

In some example embodiments, the opening size may correspond to a designated mesh classification according to a designed test procedure.

In some example embodiments, the mesh cover may be supported by a peripheral frame. The peripheral frame may have a first mounting portion. The first mounting portion may be configured to engage a corresponding second mounting portion secured to the processing chamber. A gasket may be placed between the peripheral frame and the processing chamber structure adjacent the opening to reduce test material from escaping the processing chamber and bypassing the mesh cover during a milling step.

In some example embodiments, the peripheral frame may comprise a first flange portion and the processing chamber may comprise a second flange portion. The first and second mounting portions may comprise a releasable fastener for securing the first flange portion to the second flange portion.

In some example embodiments, the support structure may be movable between a loading position in which the mill may be configured to accept introduction of the feed material therein through the input aperture and an operative position in which the mill may be configured to continuously mill the feed material introduced while in the loading position and output the milled material through the outlet aperture onto the measurement station.

Some example embodiments may further comprise a drive unit for rotating the processing chamber about a drive axis in the operative position.

In some example embodiments, the processing chamber may be oriented while in the loading position such that the input aperture is oriented substantially upward. Additionally, or alternatively, the processing chamber may be oriented in the operative position such that the outlet aperture is oriented substantially downward.

In some example embodiments, the processing chamber may be oriented while in the loading position such that the drive axis is inclined upward and in the operative position such that the drive axis is substantially horizontal.

Some example embodiments may further comprise a drive unit for driving the processing chamber about a drive axis.

Some example embodiments may further comprise a controller in communication with the measurement station, the controller comprising, or configured to communicate with, a processor and a non-transient memory for storing instructions that, when executed by the processor, cause the control unit to perform a test procedure, wherein the test procedure may comprise:

initiating the test procedure to measure the attribute of the milled material deposited on the measurement station and outputting the measurement of the milled material to the output; and terminating the test procedure when a condition is satisfied.

In some example embodiments, the controller may be configured to enable the drive unit; and to terminate the test procedure by disabling the drive unit when the condition is satisfied.

In some example embodiments, the condition may be satisfied by the measurement reaching a threshold value.

In some example embodiments, the threshold value may be a proportion of an attribute of the feed material.

In another aspect, there is provided a device for generating milling measurement data at an output, comprising: a mill having a processing chamber, the mill configured to perform, while engaged, a milling action on a feed material in the processing chamber and removing a screened undersized milled material from the processing chamber. A measurement station may be configured to measure an attribute associated with the screened undersized milled material and to output a measurement of the attribute to the output without interrupting the milling action.

In some example embodiments, the mill may be configured to continuously, regularly, irregularly or intermittently perform the milling action.

In some example embodiments, the mill may be configured to continuously, regularly, irregularly or intermittently remove the screened undersized milled material from the processing chamber.

In some example embodiments, the measurement station may be configured to detect a change in the attribute by a change in a characteristic of the processing chamber or of milled material therein.

In some example embodiments, the characteristic may be a weight of the processing chamber or the screened undersized milled material removed therefrom.

In some example embodiments, the measurement station may be a weighing station configured to collect screened undersized milled material removed from the processing chamber.

BRIEF DESCRIPTION OF THE FIGURES

Several example embodiments of the present disclosure will be provided, by way of examples only, with reference to the appended drawings, wherein.

DETAILED DESCRIPTION

Figure 1:
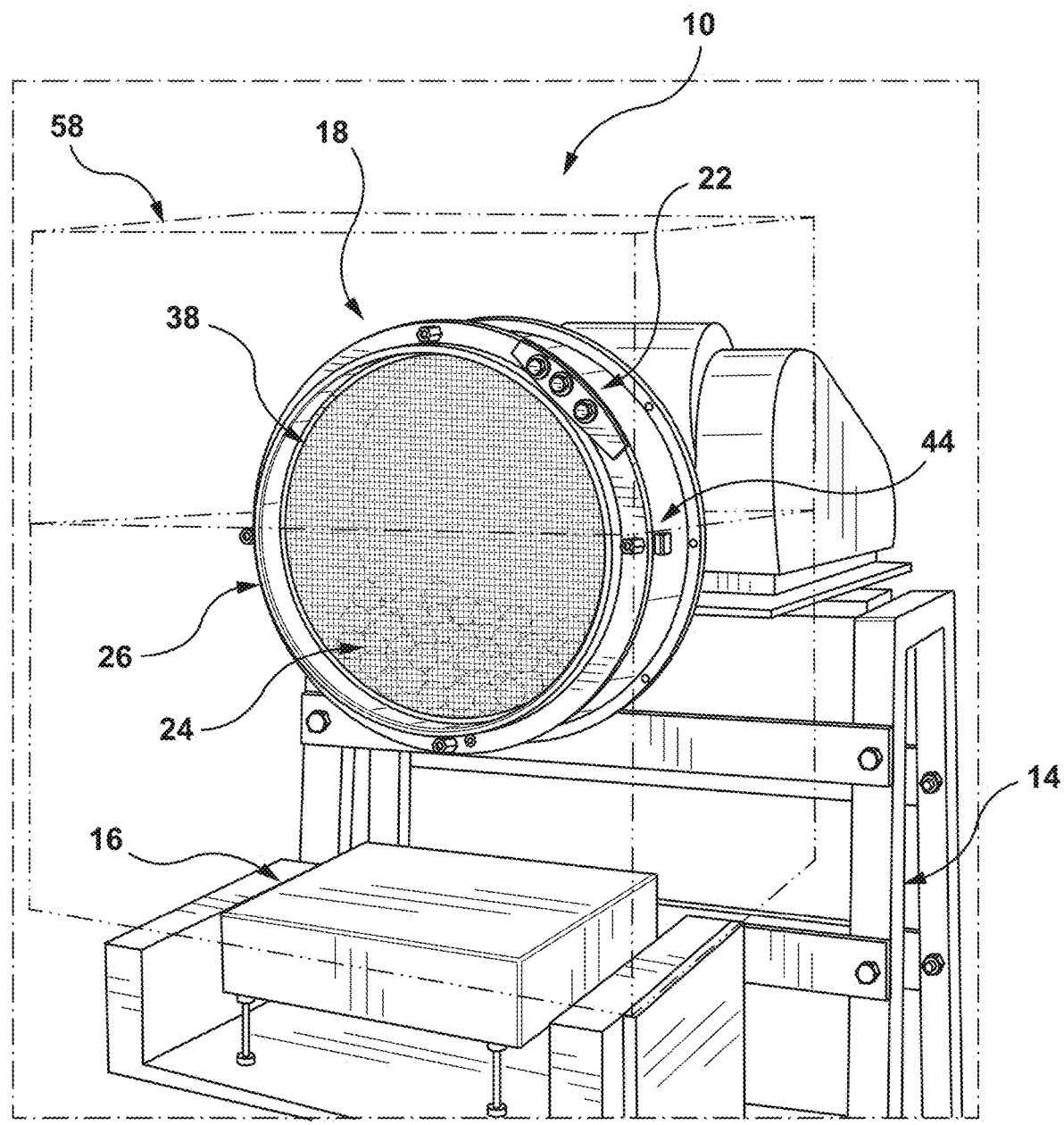
FIGS. 1 and 2 are perspective views of a device according to an example embodiment.

It should be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical, mechanical or other connections or couplings. The terms upper, lower, and vertical are intended for operative context only and are not necessarily intended to limit the invention only to those configurations or orientations. In any instance in which the disclosure refers to a single instance of an element, example embodiments may include a multiple of such elements. The term "at least one" in reference to any element is not intended to force an interpretation on any other reference elsewhere in the disclosure to a single instance of an element to mean only one such instance of the element. Furthermore, and as described in subsequent paragraphs, the specific mechanical and/or other configurations illustrated in the drawings are intended to exemplify embodiments of the invention. However, other alternative mechanical and/or other configurations are possible which are considered to be within the teachings of the instant disclosure. Furthermore, any one element, feature, structure, function, of any aspect and/or example embodiment described in the present disclosure including the figures, clauses and/or claims herein, may itself be claimed on its own or be combined with any one or more elements, features, structures, functions, and/or steps from the same or any other aspects and/or example embodiments described in the present disclosure including the figures, clauses and/and claims herein.

The term "undersized fraction" means the fraction of a test sample of feed material that is smaller in particle size than the openings of a mesh structure. Thus, when a test sample is milled or otherwise processed and delivered to a mesh screen of a designated mesh screen size or number, the undersized fraction passing through the screen may be classified by the designated screen size or number, while the "oversized" fraction does not pass through.

As will be described, example devices and methods herein may be configured to continuously remove an undersized fraction of a test sample as the test sample is processed and achieved by placing a mesh structure, or screen, on an SPI mill and by measuring the undersized fraction discharged continuously to a weighed sample collection location, until a designated threshold, or final set point, is reached. In some example embodiments, the processed sample may be collected and measured at regular intervals while the processing of the sample continues. This may be referred to as a Continuous SPI (CSPI) Test output which may be associated with the SAG Power Index to provide a calibrated CSPI Index Value. In other example devices and methods, the removal of the undersized fraction, the collection and/or the measurement of the sample may in some instances occur regularly, irregularly or intermittently while the sample is processed.

Referring to FIGS. 1 to 5, there is provided a device 10 for generating milling measurement data at an output 12. The device 10 comprises a support structure 14 and a measurement station 16 supported by the support structure 14 for measuring an attribute of a test sample milled material collected thereon, and outputting a measurement of the attribute to the output.

A mill structure 18 is supported by the support structure 14 above the measurement station 16 for, while engaged, continuously performing a milling action on a feed material, such as in this example embodiment a test sample, and depositing an undersized fraction of the test sample onto the measurement station 16 where it can measure the attribute of the undersized fraction without interrupting the milling operation.

The measurement station 16 is, in this example embodiment, a weighing structure which is configured to measure the attribute. The measurement station 16 may be configured to output a measurement of the attribute. The measurement and or the output of the attribute may occur on a continuous or regular basis, according to a designated rate, while the mill structure 18 is operating. The output may be selected from at least one of a display, a scale or an input to a computer system. Other attributes may also be monitored in addition to or in place of a weight attribute, depending on a desired test.

The mill structure 18 comprises a processing chamber 22 for holding the test sample while it performs a milling action thereon. Located in the processing chamber is a plurality of test milling balls 24 (FIG. 1).

The processing chamber has an opening 26 which serves both as an inlet aperture 28 (FIG. 3) for accepting the test material and an outlet aperture 30 (FIG. 4) for depositing the undersized fraction 32 onto the measurement station 16 (for example to be deposited into a receptacle 34 thereon). Thus, the input aperture 28 and the outlet aperture 30 are provided by the opening 26 in this instance, while in other example embodiments, the inlet and outlet apertures may be different.

The opening 26 is configured to accept a mesh cover 38 thereon, having openings of an opening size therein to deposit the undersized fraction, that is of a size less than the opening size onto the measurement station 16. The mesh cover 38 is removable and the opening size corresponds to a designated mesh classification according to a designed test procedure.

Figure 2:
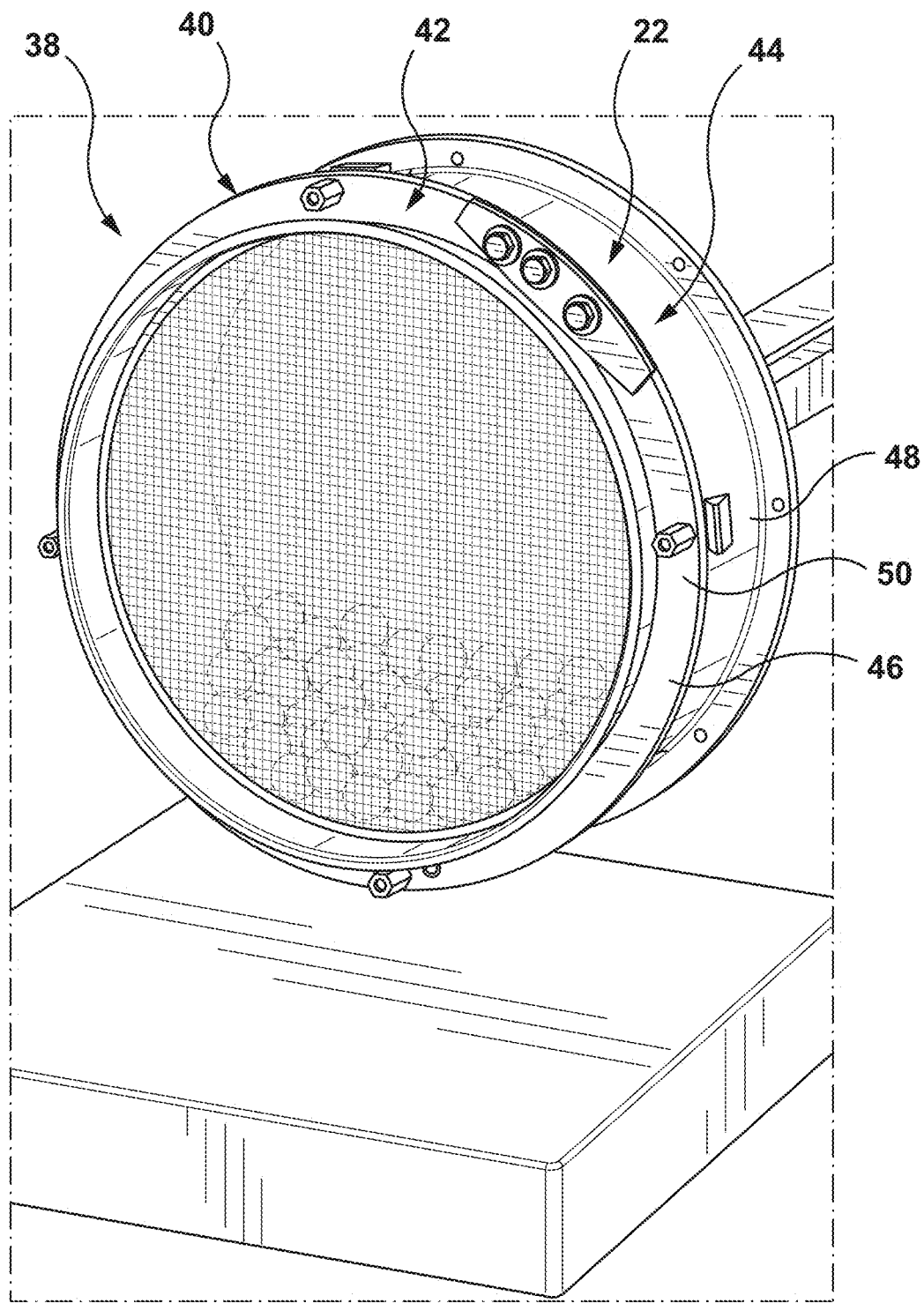

Referring to FIG. 2, the mesh cover 38 is supported by a peripheral frame 40 having a first mounting portion 42 to engage a corresponding second mounting portion 44 secured to the processing chamber 22. The peripheral frame 40 comprises a first flange portion 46 and the processing chamber comprises a second flange portion 48 wherein the first and second mounting portions 46 and 48 comprise a releasable fastener 50 for securing the first flange portion 46 to the second flange portion 48. A gasket, such as rubber ring (not shown) may be placed between the peripheral frame 40 and the processing chamber structure adjacent the opening to reduce, if not eliminate, test material from escaping the processing chamber 22 and bypassing the mesh cover 38 during a milling step.

Figure 3:
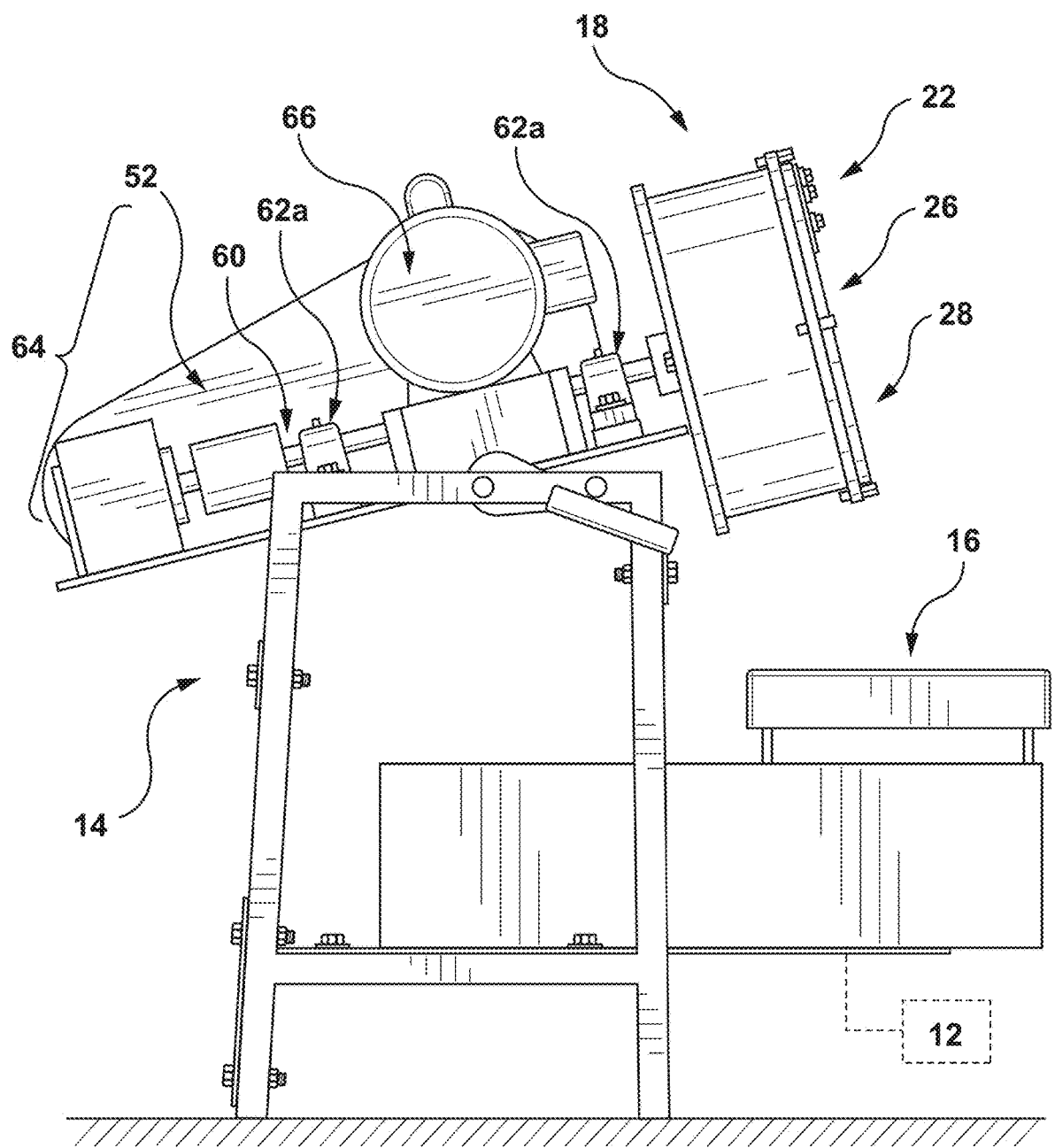
FIG. 3 is a side view of the device of FIG. 1 in a loading position.
Figure 4:
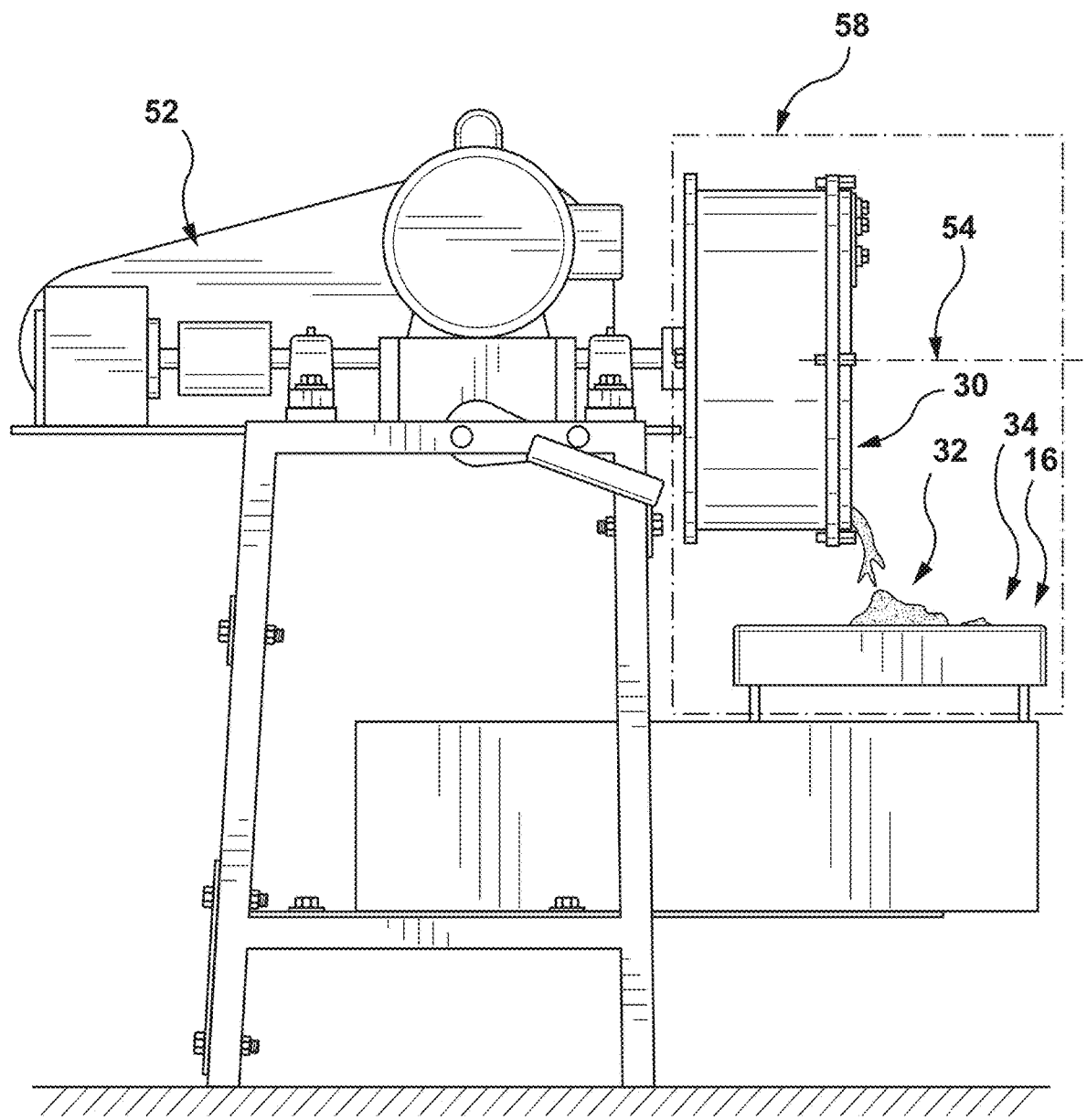
FIG. 4 is a side view of the device of FIG. 1 in an operative position.

Thus, the support structure 14 is movable between a loading position, as shown in FIG. 3, in which the mill structure 18 is configured to accept introduction of the test sample therein through the input aperture 28, and an operative position shown in FIG. 4, in which the mill structure 18 is configured to continuously mill the test sample and output the undersized fraction through the outlet aperture 30 into the receptacle 34 of the measurement station 16.

Referring to FIG. 3, the processing chamber 22 may be oriented, while in the loading position, such that the inlet aperture 28 is oriented substantially upward, and may be oriented in the operative position such that the outlet aperture 30 is oriented substantially downwardly relative to the loading position and with the outlet aperture in a position to permit the undersized fraction to pass through the openings in the mesh cover by the action of the milling balls against the test sample during operation of the mill structure 18.

A drive structure is provided at 52 rotating the processing chamber 22 about a drive axis 54 (FIG. 4) while in the operative position. The drive structure includes a shaft 60 defining the drive axis 54, which is supported by a number of bearings 62a, with the processing chamber 22 mounted on the right hand end, as shown in FIGS. 2 and 3, and a transmission section 64, which in turn is operatively coupled to motor 66.

Figure 5:
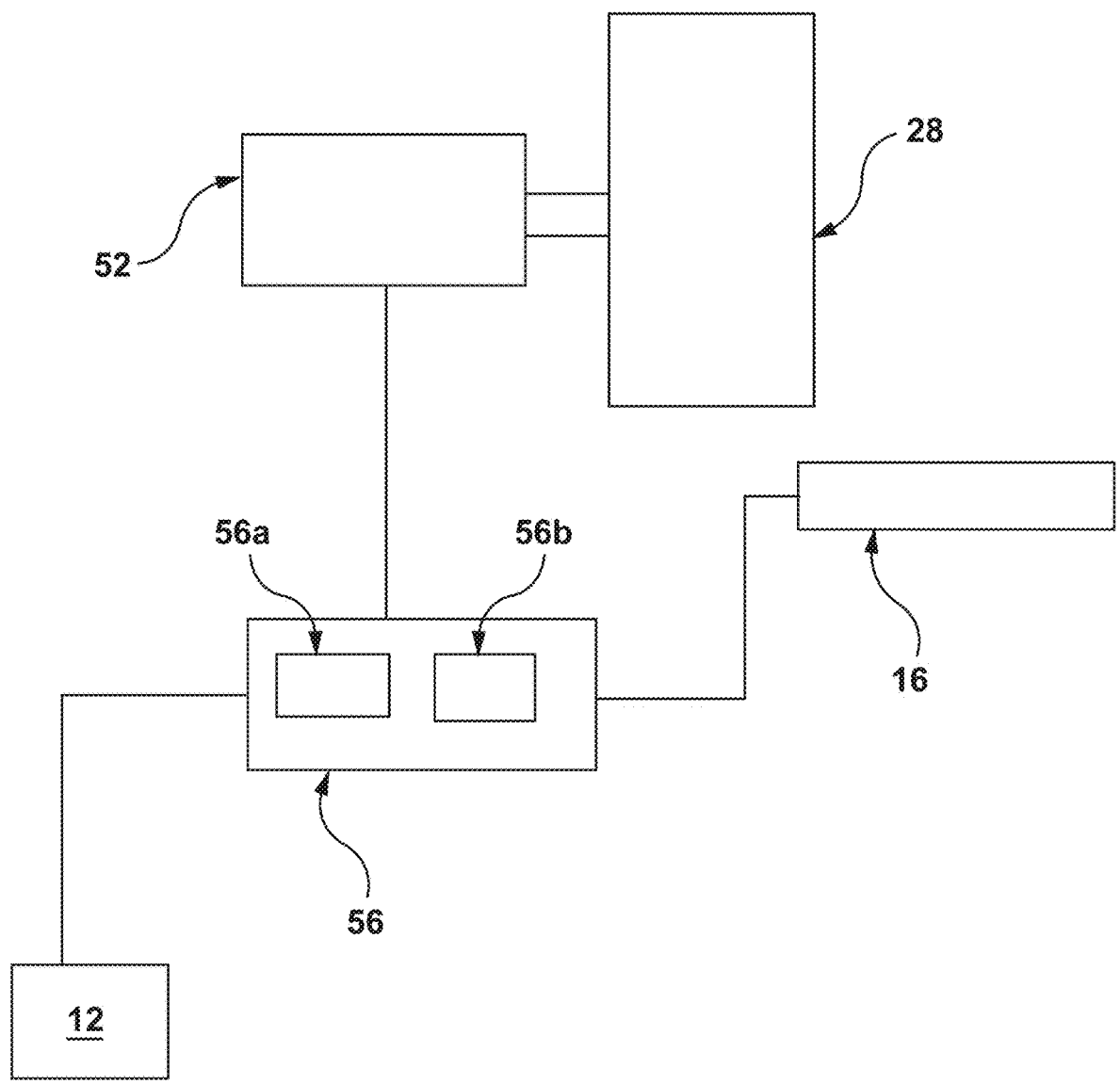
FIG. 5 is a schematic view of the device of FIG. 1.
Figure 6:
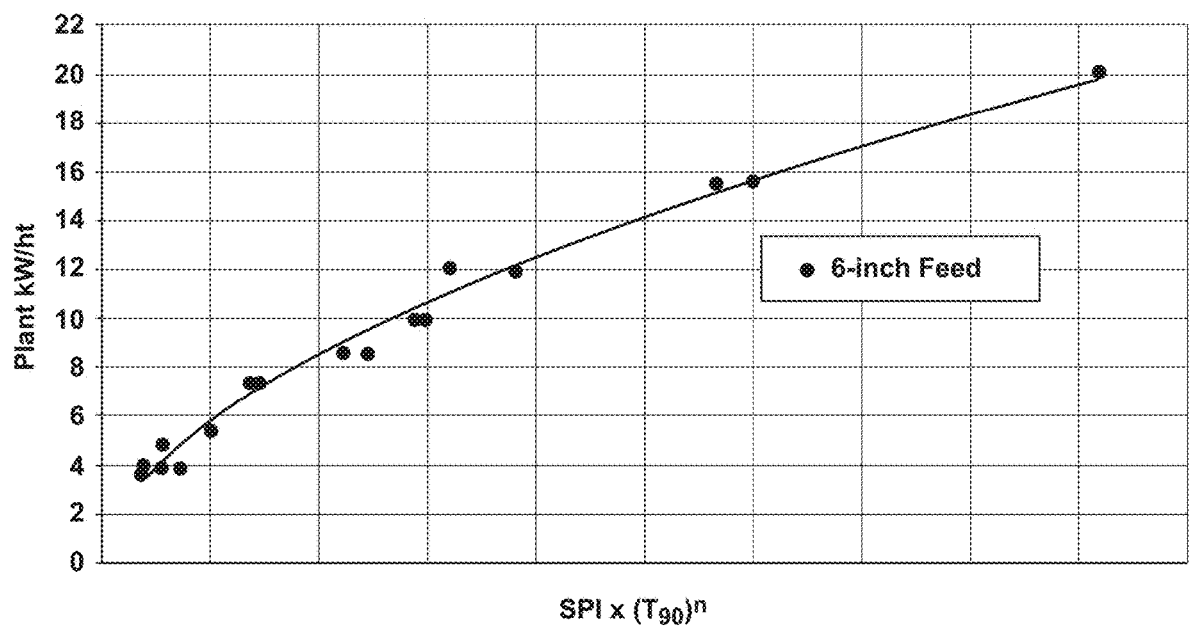
FIG. 6 is a schematic view of a graph of SPI values versus power consumption for an SPI Test.

Referring to FIG. 5, the device 10 further comprises a controller 56 which is configured to be in communication with the drive structure 52 and the measurement station 16. The controller comprises or communicates with a processor 56a and a non-transient memory 56b for storing instructions that, when executed by the processor 56a, cause the controller 56 to perform a test procedure, by:
  a) initiating the test procedure by engaging the drive structure 52 while in the operative position, so that the mill structure 18 mills the test sample without interruption;
  b) measuring the attribute of the undersized fraction deposited on the measurement station 16 and outputting the measurement to the output 12; and
  c) terminating the test procedure by disengaging the drive structure 52 when a designated condition is satisfied.

In some example embodiments, the controller 56 may or may not control the onset operation of the drive structure 5. For example, the controller 56 may rather be configured to be enabled in response to onset of operation of the drive structure 52.

In some example embodiments, the designated condition may be satisfied by the measurement reaching a threshold value, such as a designated proportion of an attribute of the test sample. In this example, the attribute may be weight of the undersized fraction expressed as a percentage of the weight of the test sample. Other designated conditions may include weight of the remaining oversized fraction in the processing chamber 22, as a percentage of the test sample.

In some example embodiments, the measurement station 16 may be configured to detect a change in weight of the processing chamber 22, as opposed to an accumulation of weight in a receptacle 34. For instance, the measurement station 16 may be configured to be located between the support station 14 and the processing chamber 22, to register a change in weight of the processing chamber 22, while allowing for power to be delivered to the processing chamber 22. While the processing chamber 22 is rotated, other example embodiments may enable motion of the processing chamber by vibration, or lateral reciprocal motion, for instance.

Thus, the device 10 may be configured in a number of ways. For instance, the processing chamber 22 may be configured to be used with meshes of different mesh classifications, depending on the test procedure, by changing the mesh cover 38, or the mesh supported by the mesh cover 38. As in the example embodiments discussed below, the mesh may be a 12-inch diameter Tyler™ 10 mesh (1.7 mm), though other mesh configurations may also be applicable such as 6 mesh (3.35 mm) or 8 mesh (2.36 mm).

In some example embodiments, the measurement station 16 may include a laboratory balance, with a receptacle 34 in the form of a test sample pan, aligned under the outlet aperture 30 to capture the undersized fraction.

In some example embodiments, the controller 56 may be provided by or include a general purpose computer communicating with an output on the laboratory balance by way of a wired or wireless computer peripheral interface.

A cover structure shown schematically at 58 in FIG. 4 may be placed over the measurement station 16 and the processing chamber 22 to effectively enclose the mill structure 18 to control dusting that may occur during a test procedure, or to prevent contamination of the accumulated undersized fraction.

Figure 7:
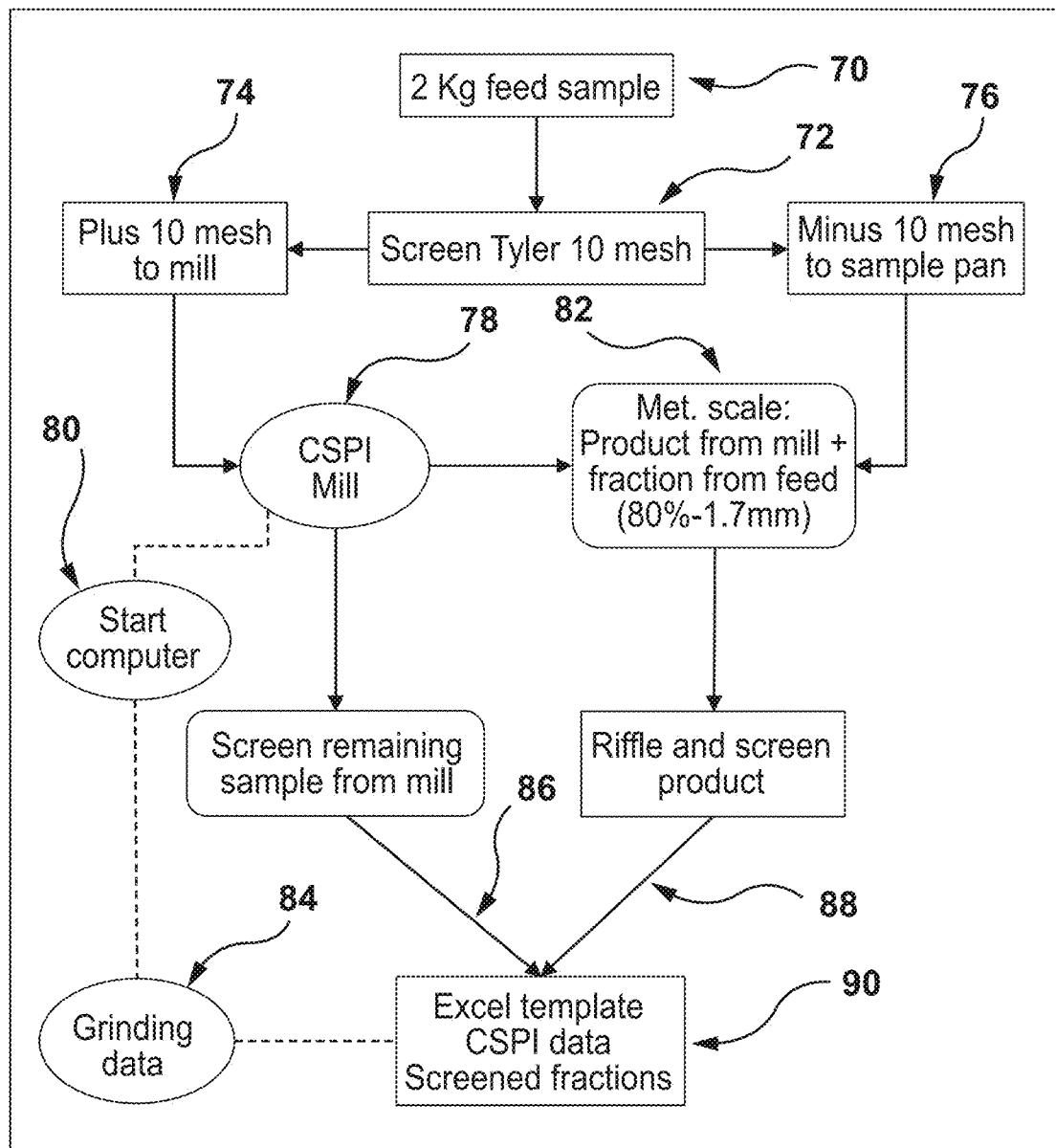
FIG. 7 is a schematic diagram of a method utilizing an example embodiment.

An example testing procedure is presented in FIG. 7. A designated sample of feed material for testing may be prepared at step 70 by selecting a 2 kg portion thereof to form the test sample, which may then be placed in the processing chamber 22, when oriented in the loading position. The mesh cover 34 may then be secured (at step 72) over the processing chamber 22 after securing the fasteners 50 between the first and second flange portions 46, 48.

Alternatively, the designated sample may be partitioned whereby the oversized (plus 10 Tyler) fraction is placed in the processing chamber (mill) and any undersized (minus 10 Tyler) fraction that may already be present in the designated sample is added to the balance at the start of the milling process, to reduce possible buffering effects, as discussed below, that may arise as a result of the undersized fraction being present in the processing chamber at the onset of the procedure.

The device 10 may then be moved with the processing chamber in the operative position, with the receptacle 34 placed in position on the measurement station 16. The cover structure 58 may then be placed over the processing chamber 22, the receptacle 34 and the measurement station 16. Thus, device 10 may be configured to that, during operation, the oversized fraction (ie larger than the 10 mesh) remains in the processing chamber 22 (at step 74) while the undersized fraction (smaller than the 10 mesh) progresses to the receptacle 34 (at step 76).

With the device 10 so prepared, the drive structure 52 may then be activated at step 78, and the controller 56 (in the form of a computer in this example) may then be enabled (at step 80) to initiate the test procedure and monitor the designated test condition, including enabling the measurement station 16 to generate weight measurements over predetermined time periods (at step 82) and to dispatch the data to the computer (at steps 84, 86, 88), to yield an output, such as an excel listing or the line on a screen or print out (at step 90) and, finally to terminate the test procedure when the designated test condition is met.

EXAMPLES

Feed material was stage crushed, as typically occurs at the mining site in a first or early stage ore processing step, to a condition in which 100% of the feed material being sized below ¾ inches (19.0 mm) (referred to as "minus ¾ inch") and with 20% being sized plus ½ inches (12.5 mm) (referred to as "plus ½ inch").

Duplicate samples were prepared from three different ore bodies with hardness ranging from an SPI time of 4 minutes (soft) to 295 minutes (hard). For each pair of samples selected, one used in a CSPI Test using an example embodiment of the device 10, and the other used in an SPI Test, with the data plotted on calibration curves.

For each ore body, a 2 kg. test sample, 100% minus ¾ inch, having a proportion of 20% plus ½ inch, was screened. The "plus" 0.067 inch (1.7 mm) material (that is material having a particle size in excess of 1.7 mm) was placed in the processing chamber 22 together with the milling balls 24. The mesh cover 38 was provided with a Tyler™ 10 mesh screen (available from wstyler.com) and positioned and secured in place in the opening 26. The processing chamber was then moved to the operative position and the measurement station 16, receptacle 34 (with the remaining minus 0.067 inch (1.7 mm) feed) and the cover structure 58 were also placed in position. The controller 56 was programmed to collect information every second and stop the mill structure 18 at a set point when the discharged undersized fraction reached around 1600 g (~80% of the test sample). The "minus" 0.067 inch (1.7 mm) undersized fraction material was obtained after milling and thereafter collected from the screen in the receptacle 34. These steps were repeated for a number of test samples.

While the mesh cover 38 did not show significant damage for the first fifty tests performed on the mill structure 18, the mesh cover 38 was changed to ensure consistent passage sizes to reduce a possibility of larger un-sized particles passing through the mesh cover 38.

Figure 8A:
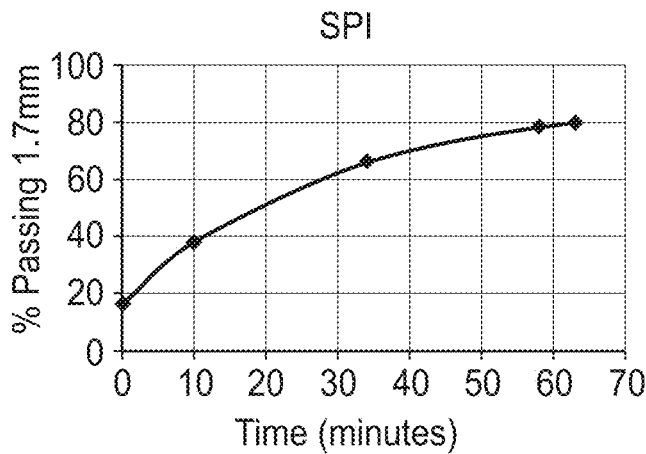
FIGS. 8a and 8b are respective plots of outputs of a SPI Test, and a CSPI Test utilizing an example embodiment.
Figure 8B:
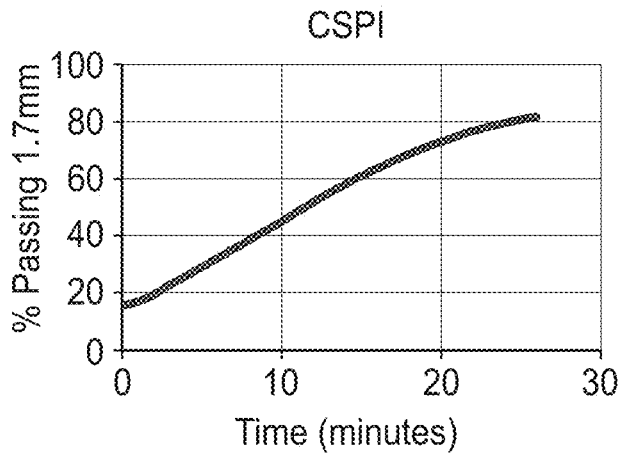

FIGS. 8a and 8b present an example of results of acquired data collected for a standard SPI Test (FIG. 8a) and a CSPI Test procedure (on a first ore body from South America as shown in table 1), using an example of the device 10 (FIG. 8b). In the case of the CSPI Test, the accumulating weight of the undersized fraction was repeatedly measured at one second increments over the test procedure operating period. FIG. 8b shows a relatively smooth and continuous graph. FIG. 8a, in contrast, shows four data points after four separate reset iterations.

Figure 9:
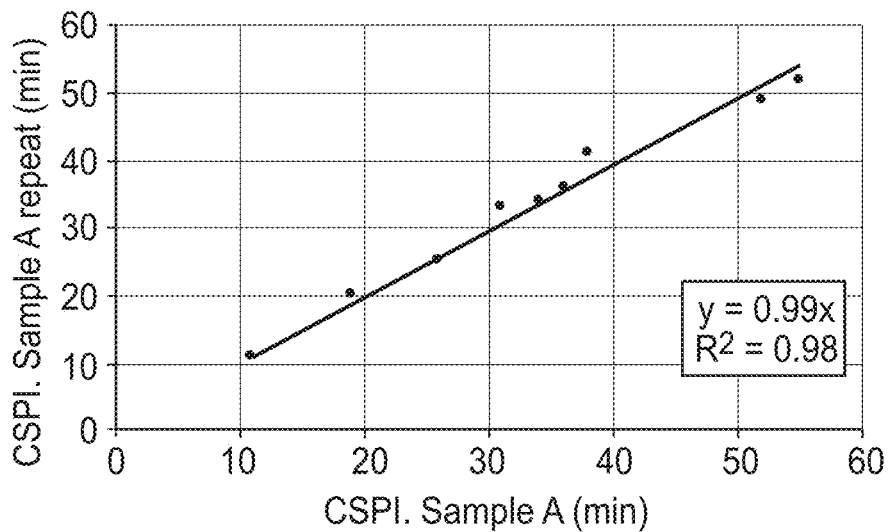
FIG. 9 is a plot of time versus time for duplicate methods utilizing an example embodiment.

In another example, pairs of the same samples of the first (South America) ore body were carried out on an example of the device 10 to determine the repeatability, with the results presented in FIG. 9, with y at 0.99x and $R^2$ at 0.98. The results estimated a standard error to be 1.9, indicating very good operational repeatability.

Figure 10:
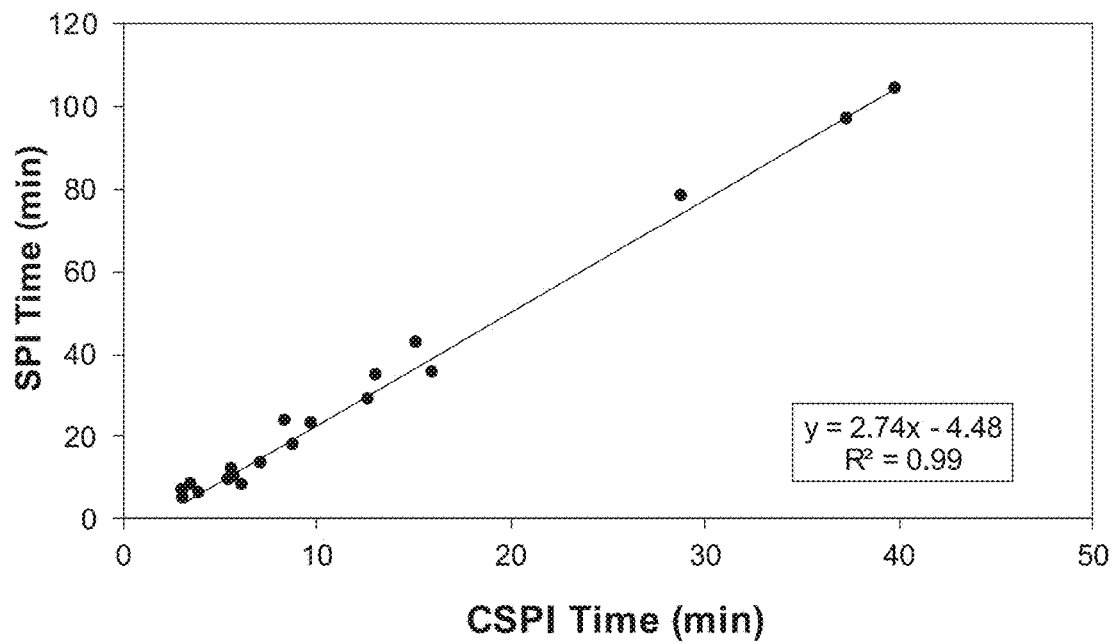
FIGS. 10 to 12 are comparative time-time plots for a method utilizing an example embodiment.

In another example, an example of the device 10 was used in a CSPI Test, in parallel with an SPI Test, on samples from a second ore body (an iron ore deposit), with results shown in FIG. 10 in which the X axis is time using the CSPI Test to reach a weight threshold of 80% of the test sample, and the Y axis is the is time using the SPI Test to reach a weight threshold of 80% of the test sample, with y=2.74x−4.48 and $R^2$ at 0.99. The sample SPI times show a hardness range from 4 minutes to 104 minutes, that is to reach the designated threshold of 80 percent passing through 10 mesh (1.7 mm), while the CSPI Test shows a hardness range from 3 to 40 minutes. In this case, continuous removal of the undersized fraction (smaller than 1.7 mm) through the screen reduces (if not prevents) the undersized fraction from buffering the milling balls, as may occur if the undersized fraction accumulates in the processing chamber to an extent to cause significant quantities of the undersized fraction to be present between the balls and respective instances of the oversized fraction at the point of impact there between, to reduce the effectiveness of the impact, and thus reduce a milling function efficiency, thus causing a resulting reduction of milling rate and an increase in needed processing time.

Figure 11:
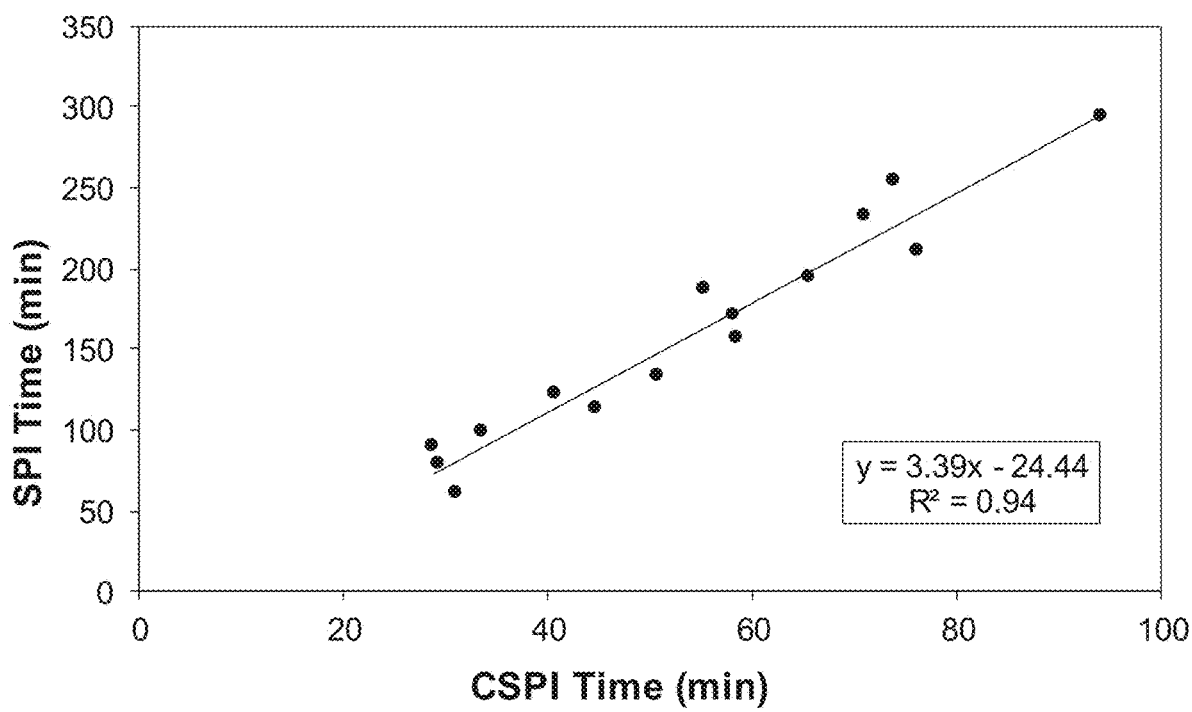

FIG. 11 is a plot for samples from of a third ore body, in this case of "hard ore" within the ore body (meaning having a hardness of an SPI time greater than 150 minutes) in which the hardness, SPI time ranges from 60 minutes to 293 minutes with a standard error of 17, with relatively more variability, with y=3.39x−24.44 and $R^2$ at 0.94.

Figure 12:
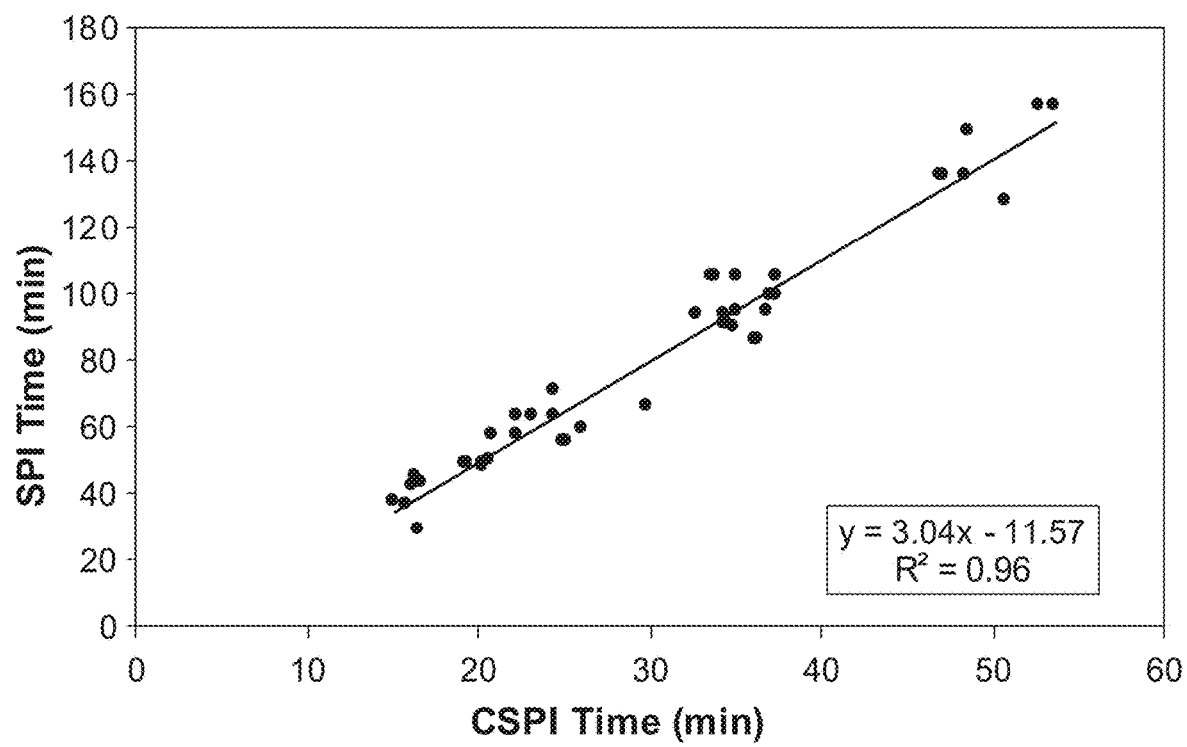

FIG. 12 presents the data for test samples from a third medium hard deposit. The SPI time ranges from 29 minutes to 157 minutes with a standard error of 7.2, with y=3.04x−11.57 and $R^2$ at 0.96.

Figure 13:
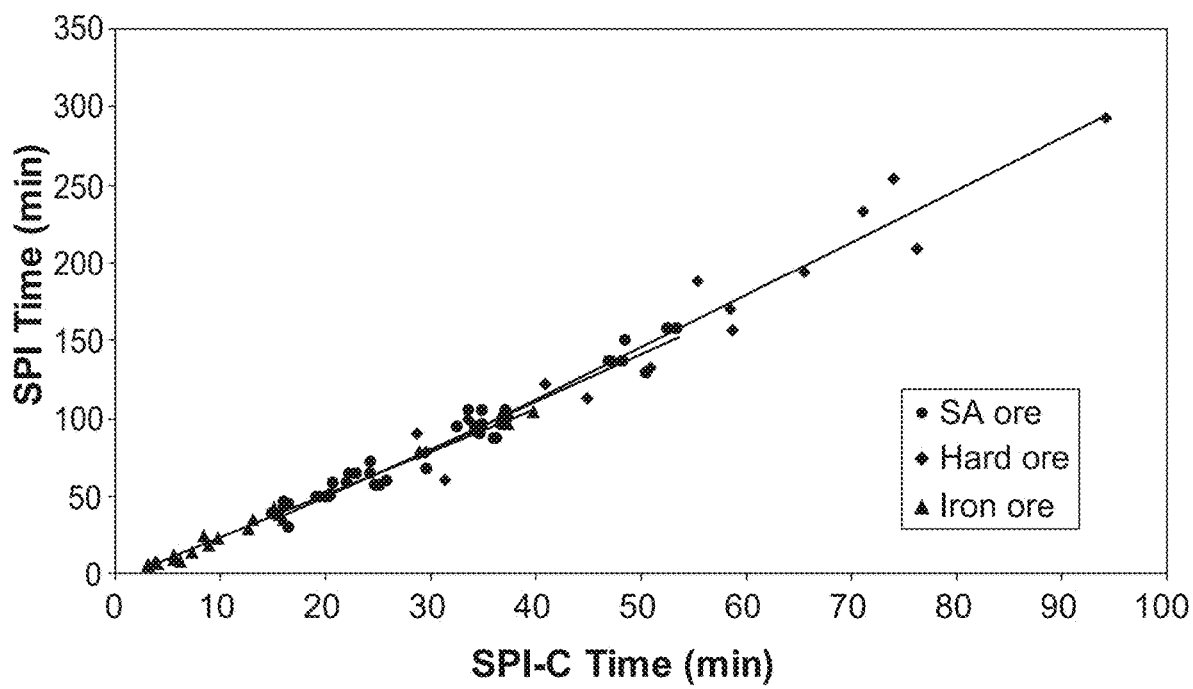
FIG. 13 is a comparative plot of the time-time plots of FIGS. 9 to 11.
Figure 14:
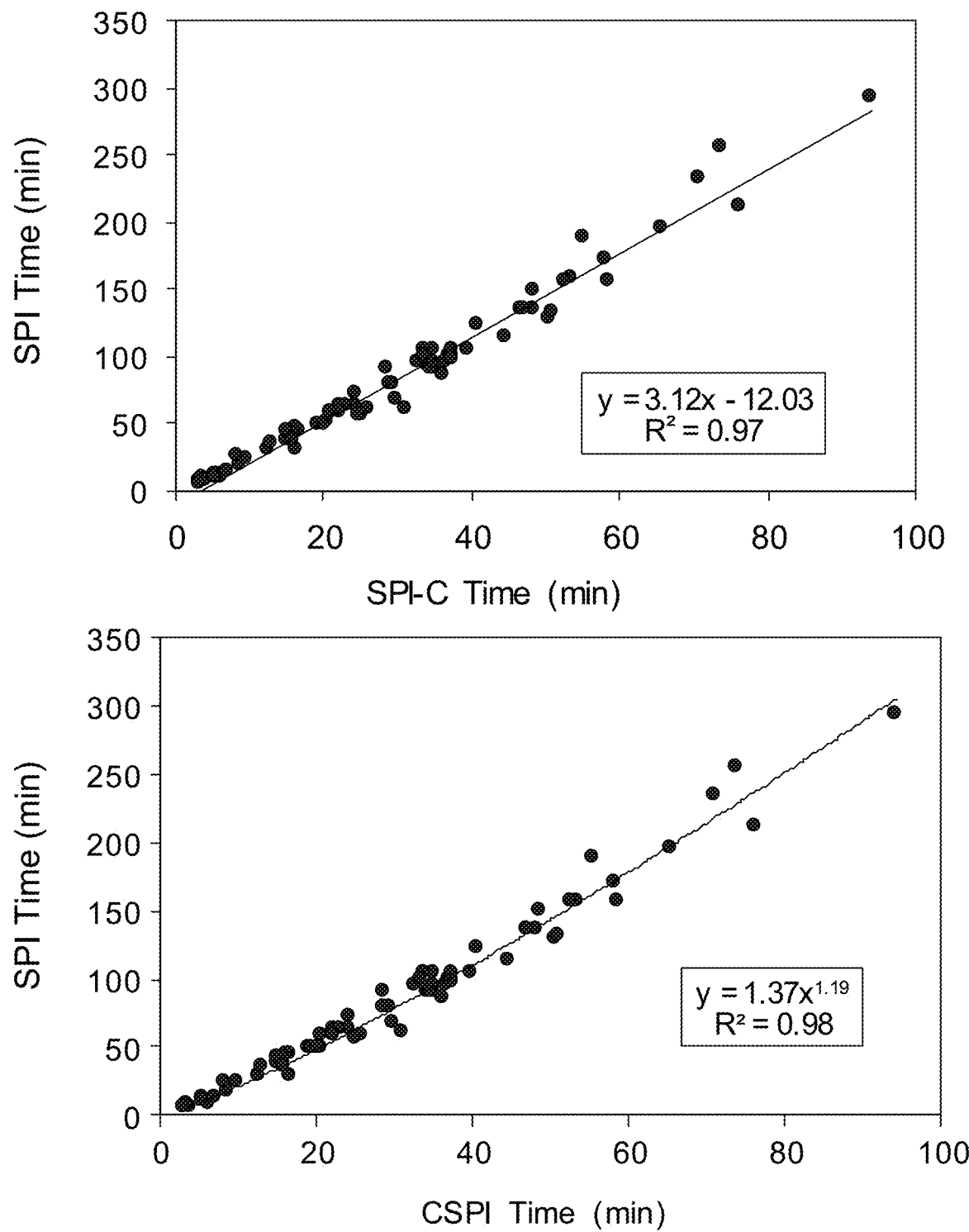
FIG. 14 is a comparative plot of time-time plots for yielding a generic equation for a test sample.

All test data from seventy eight pairs of test samples from the first, second and third ore bodies is displayed in FIG. 13, to observe an overall outcome (when two general equations are possible, and which may be used to calculate the SPI from the CSPI. The hardness variability ranges from soft to hard (~4 minutes to 293 minutes). More useful data may be obtained by evaluating each ore deposit separately and work with the grindability of that range. This approach may lead to a better SPI/CSPI relationship specific to a particular deposit.

The 12 inch diameter Tyler™ 10 mesh was found to be strong with little variations but was changed three times during the investigations to eliminate uncertainties.

The collected data in FIGS. 9, 10, 11, 12 shows that each ore body may present a different gradient which may provide greater insight into the progressing milling process and how it may be optimized. This demonstrates that the CSPI Test may be repeatable and may be calibrated to an accepted test while providing significantly improved granularity in results. This approach may thus yield a parity curve for each mine deposit tested within the range of hardness as representative of that ore body, thus providing the basis for establishing values for each of the variables for an equation for the ore body.

TABLE 1

| Identification | Linear Equations. Index, Time in min. | $R^2$ | Std Dev | Std Error | SPI Test Range min | SPI Test Range max | No. of Samples |
| --- | --- | --- | --- | --- | --- | --- | --- |
| An Iron Ore Company | Spi Time = 2.74 * CSpi Time − 4.48 | 0.99 | 24.3 | 2.8 | 4 | 104 | 19 |
| A Hard Ore Mine | Spi Time = 3.39 * CSpi Time − 24.44 | 0.94 | 73.0 | 17.0 | 60 | 293 | 15 |
| A South American Ore body | Spi Time = 3.04 * CSpi Time − 11.57 | 0.96 | 36.1 | 7.2 | 29 | 157 | 44 |
| Overall | | | | | | | |
| Generic Equation (Linear) | Spi Time = 3.12 * CSpi Time − 12.03 | 0.97 | 51.6 | 11.6 | 4 | 293 | 78 |
| Generic Equation (Power) | Spi Time = 1.37 * {CSpi Time}$^{1.19}$ | 0.98 | 51.6 | 11.6 | 4 | 293 | 78 |

Table 1 presents a summary of the surveys of the three ore bodies tested from three different locations. Linear equations are presented as the best fit within each ore deposit and an overall equation, linear and power, to fit the data from the three deposits.

Comparative data shows that the CSPI test procedure may be used as a modified form of the standard SPI, and may involve fewer steps, a relatively shorter time to complete a test, with reduced manual errors arising such as with the handling of the feed sample at each reset iteration.

The output data provided by the CSPI Test may thus provide a complement to the Standard SPI Test, with a relatively faster turn-around time on more competent (hard) ore while saving the time involved in the several reset iterations, and removing or reducing errors that would otherwise arise with such reset iterations.

The CSPI Test may be ore body specific in some cases where a calibration curve is established for the ore body being investigated.

Some example embodiments may thus provide a model of the grinding behaviour of the ore sample over time. The CSPI test procedure may allow the grindability to be assessed at a higher frequency (grams per second through the screen) giving rise to comparatively many data points as compared to the SPI with four (or comparatively few) data points. This may allow for the calculation of possible kinetics to assess the grinding behavior of the sample. (For example, the grinding pattern may confirm a rate constant or give rise to a spread of rate constants for the sample under consideration). Grindabilty, as indicated by one or more K values, may demonstrate the degree of heterogeneity of the ore body under consideration. The value "K" is a kinetic constant for each sample which may be incorporated in grinding models to assist in possible plant designs.

Figure 15:
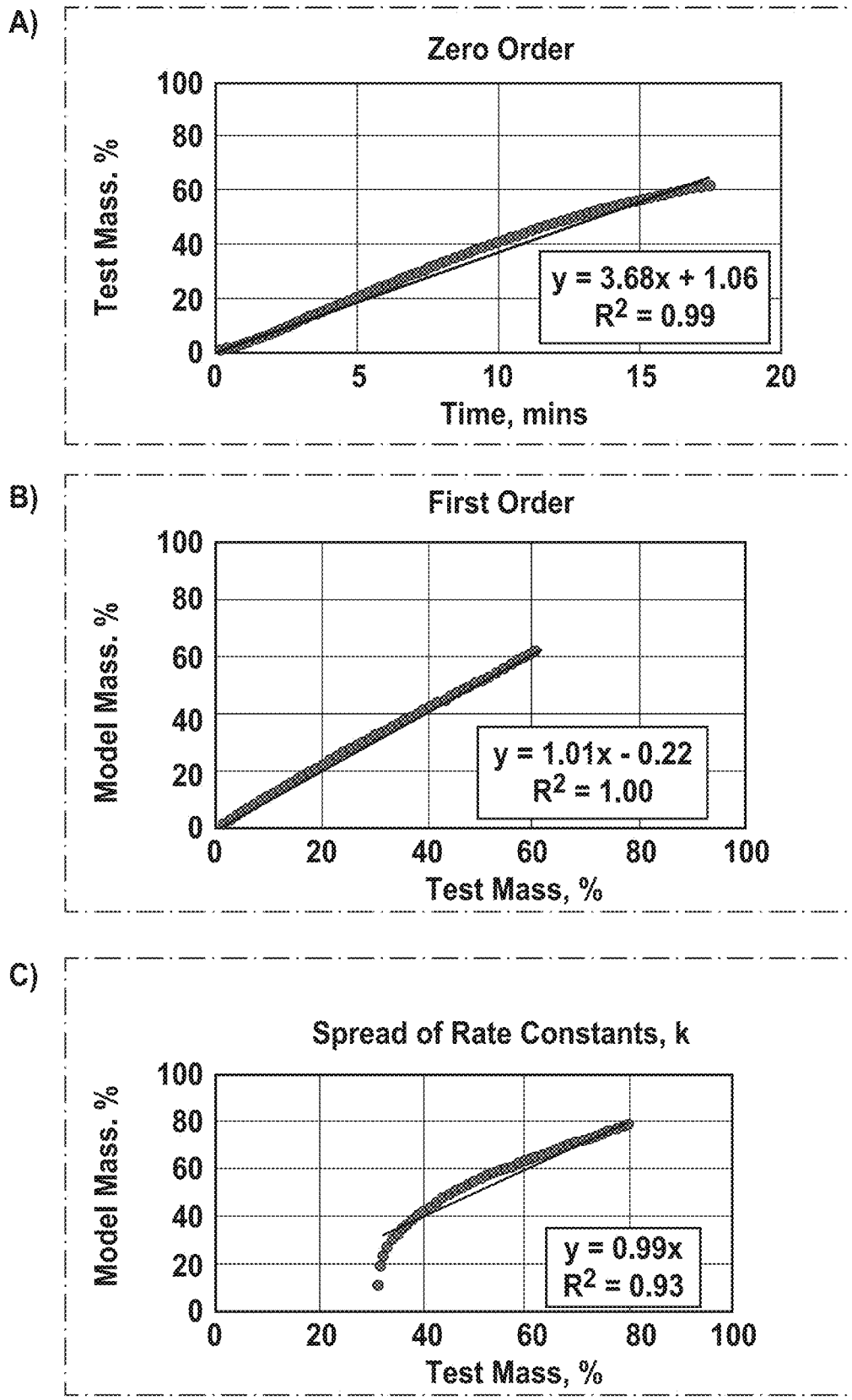
FIGS. 15, 16, 17, and 18 are time-percent mass plots for use in determining a kinetic constant.
Figure 16:
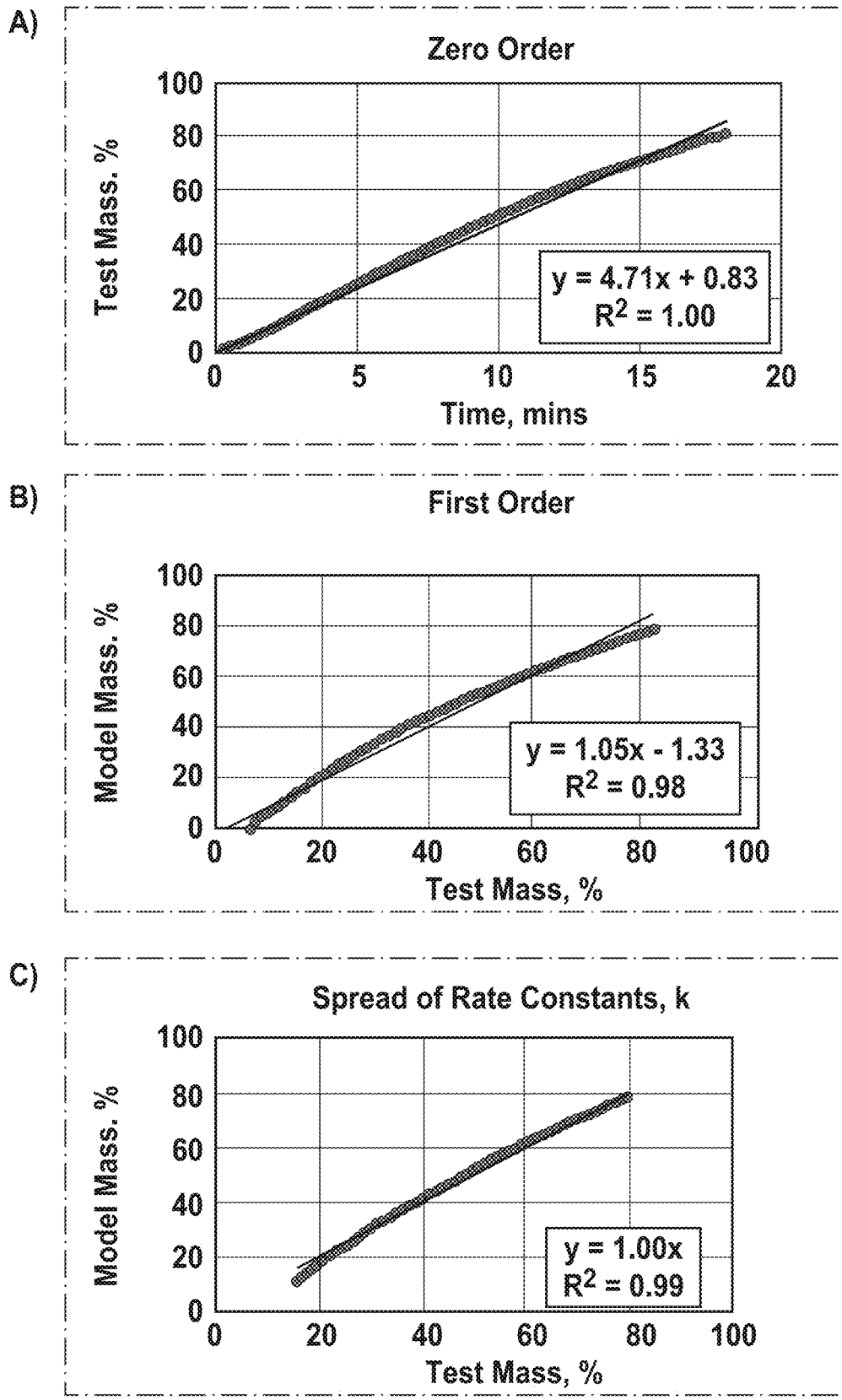
Figure 17:
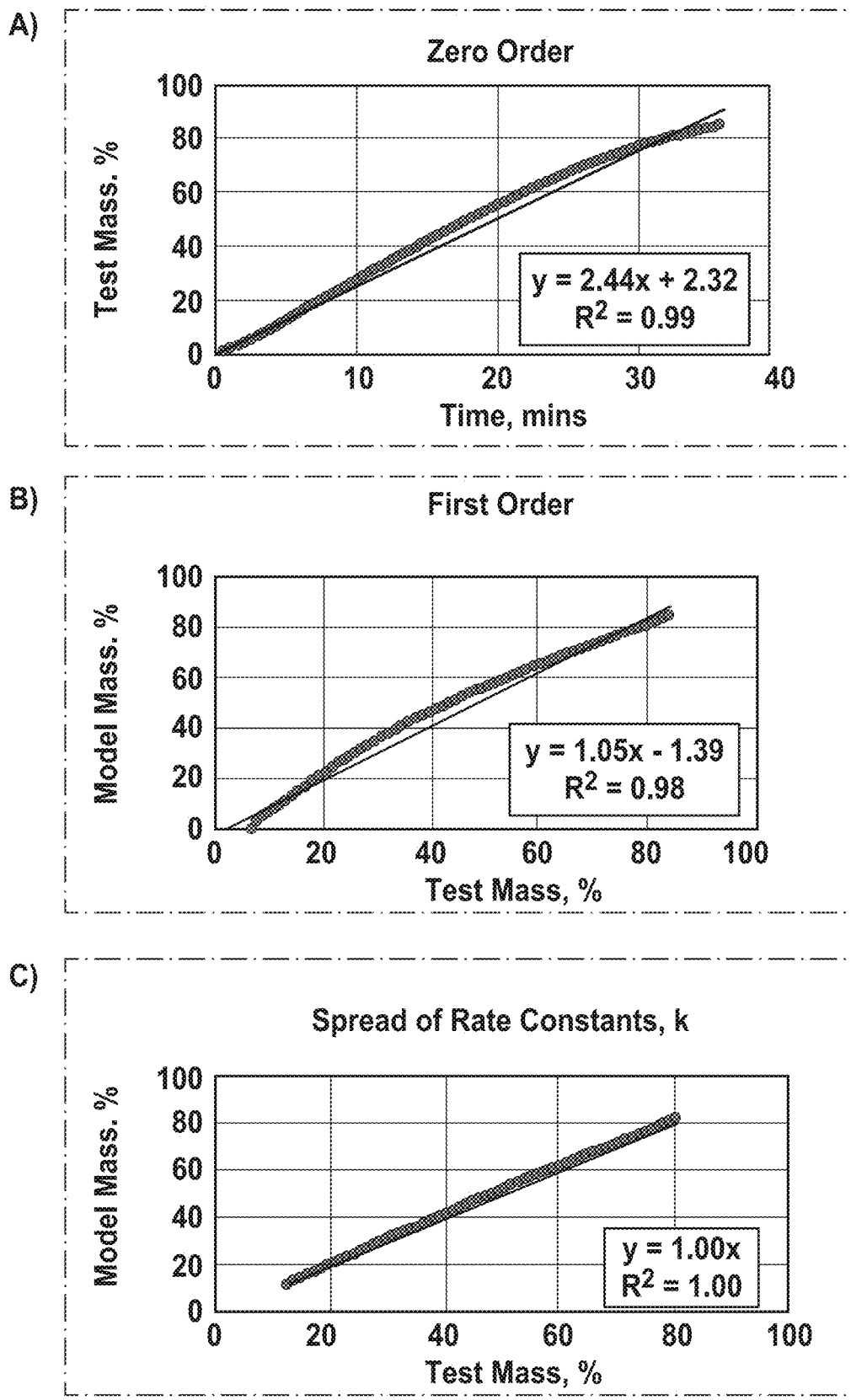
Figure 18:
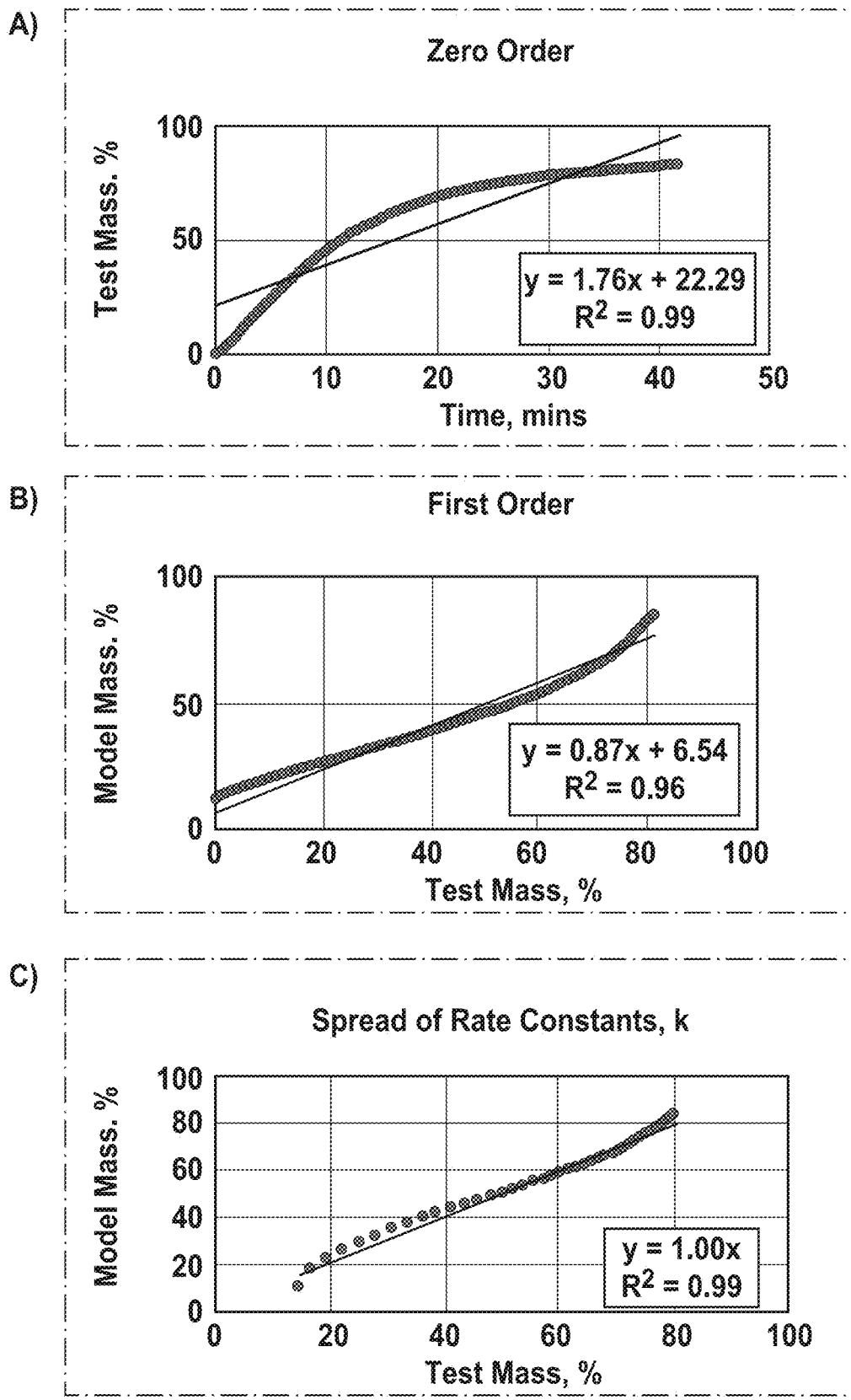

For example, a grinding behaviour of a sample under investigation may be assembled by fitting a rate equation. As seen in FIGS. 15, 16, 17, and 18, two models were attempted namely a first order rate equation, and an equation that may relate an average k value to describe a spread of k at 90% grind. The first order model describes the actual sample that is milled after removing the percentage passing the grind size. The model that defines a spread of rate constant, k average, may have an associated factor that describes the spread of the k at a set recovery of 90%. The grinding behaviour may give an indication of the friability—heterogeneity of the sample. For example, FIGS. 15 and 16 are two samples with a CSPI time of about 16 minutes but exhibit different grindability (milling) behaviour. FIG. 15 is closer to a first order, whereas FIG. 16 may be described as having a spread of k values. FIGS. 17 and 18 may be considered as having a spread of k values over that of a first order fit. The spread of the k may define a more heterogeneous ore whereas a constant k from the first order fit may define a sample that is closer to being more homogeneous in its hardness behaviour. Other models may also be considered to describe or characterize the rock sample, and define or specify an ore body under consideration.

The present disclosure may be implemented advantageously on an electronic device within a computing and communications environment that may be used for implementing the devices and methods disclosed herein.

In some example embodiments, the electronic device typically comprises a processor, which may be and/or function as the processor 56a of the controller 56, and a memory, which may be and/or function as the memory 56b of the controller 56. In some cases, the electronic device may further comprise any one or more of a bus to connect components of the electronic device, a network interface, a mass storage device, a video adapter and/or an input and/or output (I/O) interface.

The electronic device may utilize all, or only a subset of such components, and levels of integration may vary from device to device.

The electronic device may comprise multiple instances of such components, such as, by way of non-limiting example, multiple processors, memories, transmitters and/or receivers.

The processor may be one or more central processing units (CPUs), including without limitation, either or both of general and specific microprocessors, and may further include specialized processors such as a graphics processing unit (GPU), digital signal processor (DSP), or other such processor, including without limitation, dedicated hardware circuits for performing a specific functionality.

The processor provides functions by executing instructions, codes, computer programs and/or scripts, which it accesses from the memory and/or a mass storage device in the form of software and/or firmware and/or in any combination of hardware, software and/or firmware. The functions may be provided by a single dedicated processor, by a single shared processor, or by a plurality of individual processors, some of which may be shared or distributed.

The functions provided, including without limitation, functional blocks labelled in the drawings and described herein as "functions", "blocks", "modules", "processors" and/or "controllers", may be provided through the use of dedicated hardware, as well as hardware capable of executing software, but should not be understood to refer exclusively to such hardware.

Such instructions, codes, computer programs and/or scripts may be implemented in a high-level procedural or object-oriented programming language, a markup language, in source, object and/or assembly code and/or machine language. Such code or language may be compiled or interpreted. In particular, the foregoing description of one or more specific examples does not limit the present disclosure to any particular computer programming language, operating system, system architecture or device architecture.

While the instructions may be discussed in the present disclosure as being executed by a processor, in some examples, the instructions may be executed serially, simultaneously or in parallel.

The memory may comprise any type of non-transitory volatile and/or non-volatile system memory, readable by the processor, such as, without limitation, random access memory (RAM), used to store volatile data and perhaps to store instructions, including without limitation, static RAM (SRAM), dynamic RAM (DRAM), synchronous DRAM (SDRAM), read-only memory (ROM), a non-volatile memory device (which typically has a small memory capacity relative to the memory capacity of mass storage devices), such as, without limitation, programmable ROM (PROM), erasable PROM (EPROM), electrically erasable PROM (EEPROM), flash memory devices, or any combination thereof. Access to either both of RAM and/or ROM is typically faster than to mass storage devices. In some examples, the memory may be implemented as and/or comprise one or more buffer circuits, such as, without limitation, a latch or a flip flop. In some examples, the memory can be supplemented by, or incorporated in, any one or more of an application-specific integrated circuit (ASIC), field-programmable gate array (FPGA) and/or DSP.

In some example embodiments, the processor may receive instructions and/or data from RAM and/or ROM.

In some example embodiments, the memory may include more than one type of memory, such as, by way of non-limiting example, ROM for use at boot-up and DRAM for program and/or data storage for use while executing instructions. In some example embodiments, the memory may serve as a cache or interim storage medium for storing data that otherwise would be stored in and accessed from the mass storage device.

In some example embodiments, the memory may be accessed directly by the processor, or indirectly along a bus, a network interface and/or an I/O interface.

In some example embodiments, the bus may be any one or more of any type of several bus architecture, including without limitation, a processor bus, a memory bus or memory controller, a peripheral bus, a video bus, a hard drive controller, and/or an I/O controller.

The network interface may be a wired network interface to connect to a network, a wireless network interface, including, without limitation, a radio access network interface for connecting to other devices over a radio link. In some examples, the network interface may take the form of a network connectivity device, such as a modulator-demodulator (modem), a modem bank, a network card, such as, without limitation, a local area network (LAN) card, such as an ethernet card or a token ring card, a wireless LAN (WLAN) card, a radio transceiver card, such as, without limitation, a code division multiple access (CDMA) or global system for mobile communications (GSM), third generation (3G), including without limitation, general packet radio service (GPRS), universal mobile telecommunications system (UMTS), enhanced data rates for GSM evolution (EDGE), CDMA2000, wideband CDMA (W-CDMA), fourth generation (4G), including without limitation, long term evolution (LTE), WiMAX, fifth generation (5G) and/or later wireless technology card, a fiber distributed data interface (FDDI) card, a wireless local area a universal serial bus (USB) interface card, and/or some other serial interface card, a wireless interface and/or card, including without limitation, WiFi, Bluetooth, near field communications (NFC) and/or another well-known network device or interface.

The network interface allows the electronic device to communicate with a remote entity, such as a network such as, without limitation, an Internet or one or more intranets and/or a remote entity connected to such a network, by which the processor might receive information therefrom and/or output information thereto.

In some example embodiments, the network interface may comprise one or more transmitter and/or receiver for wireless or otherwise transmitting and/or receiving signals respectively.

In some example embodiments, the network interface may be accessed directly by the processor, or indirectly along a bus and/or another network interface and/or an I/O device.

In some example embodiments, at least one of the measurement station 16 and the drive structure 52 may be coupled to the electronic device by at least one of the bus, network interface and/or the I/O interface.

The mass storage device may comprise any type of non-transitory storage device, such as, without limitation, an internal or removable drive, such as, without limitation, a magnetic tape drive, a magnetic card or disk drive, a hard disk drive, an optical disk drive, including without limitation, a video disk drive, a CD-ROM disk and/or DVD-ROM disk, a magneto-optical disk drive and/or a solid state drive.

The mass storage device may be configured to store instructions, data and/or other information, and to make such instructions, data and/or other information accessible to the processor. In some example embodiments, the mass storage device may be integrated with a heterogeneous memory.

In some example embodiments, the mass storage device may be accessed directly by the processor, or indirectly along a bus, a network interface and/or an I/O interface.

The mass storage device may generally perform storage tasks compatible with higher latency but may provide lesser or no volatility. In some examples, the mass storage device may be used as an overflow storage device if the memory is not large enough to hold all working data.

The video adapter and/or I/O interface provide an interface to couple the electronic device to an internal and/or external I/O device. By way of non-limiting example, an I/O device may comprise a display coupled to the video adapter and/or a printer, a video monitor, liquid crystal display (LCD), light-emitting diode (LED) display, a touch screen display, a keyboard, keypad, switch, dial mouse, trackball, trackpad, speaker, headset, headphone, voice recognizer, card reader, paper tape reader, fingerprint, iris and/or facial scanning device, and other well-known I/O devices coupled to the I/O interface.

In some example embodiments, the I/O device may be accessed directly by the processor, or indirectly along a bus, a network interface and/or an I/O interface.

In some example embodiments, the electronic device may be an element of communications network infrastructure.

In some example embodiments, the electronic device may be a device that connects to the network infrastructure over a radio interface, such as a mobile telephone, smartphone, personal digital assistant (PDA) or other handheld device, personal computer (PC), audio-visual (AV) terminal, television, video monitor and other devices that may be classified as a user equipment (UE).

In some example embodiments, the electronic device may be a machine type communications (MTC) device (also referred to as a machine-to-machine (M2M) device), or another such device that may be categorized as a UE despite not providing a direct service to a user.

In some example embodiments, the electronic device may also be referred to as a mobile device, a term intended to reflect devices that connect to a mobile network, regardless of whether the device itself is designed for, or capable of, mobility.

When the electronic device is a network infrastructure element, the radio access network interface may be omitted for nodes or functions acting as elements of the PLMN, other than those at the radio edge of a network.

When the electronic device is infrastructure at the radio edge of the network, both wired and/or wireless network interfaces may be provided.

When the electronic device is a wirelessly-connected device, the radio access network interface may be present and may be supplemented by other wireless interfaces, such as, without limitation, WiFi, bluetooth and/or NFC network interfaces.

In some example embodiments, the electronic device may be a stand-alone device, while in other example embodiments, the electronic device may be resident within a data center. As will be understood by those having ordinary skill in the art, a data centre is a collection of computing resources (typically in the form of services) that can be used as a collective computing and/or storage resource. Within a data centre, a plurality of services can be connected together to provide a computing resource pool upon which virtualized entities can be instantiated. Data centers can be coupled together to form networks consisting of pooled computing and/or storage resources coupled to one or another by connectivity resources.

The connectivity resources may take the form of physical connections such as ethernet and/or optical communications links, and in some instances, may include wireless communication channels as well. If two different data centers are coupled by a plurality of different communication channels, the links can be combined tougher using any of a number of techniques, including without limitation, the formation of link aggregation groups (LAGs).

It should be understood that any or all of the computing, storage and/or connectivity resources (along with other resources within the network) may be divided among different sub-networks.

Thus, the electronic device may be, in some example embodiments, a programmable processing system suitable for implementing or performing one or more of the apparatus(es) or method(s) of the present disclosure. Those having ordinary skill in the relevant art will appreciate that it is understood that typically, the electronic device will have sufficient processing power, memory and/or mass storage resources and/or network throughput capability to adequately handle the workload imposed upon it by such apparatus(es) and/or method(s).

The apparatus(es) of the present disclosure may in some example embodiments be implemented in a computer program product tangibly embodied in a machine-readable storage device, including without limitation, the memory and/or mass storage device, for execution by the processor and the method(s) and/or action(s) of the present disclosure can be performed by the processor executing one or more instructions, whether or not in a program thereof, to perform functions of the disclosure, by operating on input data and/or generating output data.

In some example embodiments, information comprising the instructions and/or data to be acted upon by the processor, may be received and/or outputted by the processor in the form of a computer data baseband signal and/or a signal embodied in a carrier wave. In some example embodiments, the information may be exchanged between the electronic device and a network.

In some example embodiments, the signal may propagate in or on the surface of an electrical conductor, in a coaxial cable, in a waveguide, in an optical medium, including without limitation, an optical fiber, or in the air or free space. The information contained in the signal may be ordered according to different sequences, as may be desirable for either processing and/or generating the information, and/or in transmitting and/or receiving the information. The signal, whether baseband or embedded in a carrier wave, or other types of signals currently used or hereafter developed, and referred to herein as the transmission medium, may be generated according to several well-known methods.

Thus, an article of manufacture for use with an apparatus of the present disclosure, such as a pre-recorded storage device or other computer-readable medium, including program instructions recorded thereon, or a computer data signal carrying computer-readable program instructions may direct an apparatus of the present disclosure to facilitate the practice of a method of the present disclosure. It is understood that such apparatus(es), articles of manufacture and/or computer data signals also come within the scope of the present disclosure.

The present disclosure describes what are considered to be practical example embodiments. It is recognized, however, that departures may be made within the scope of the invention according to a person skilled in the art. Further, the subject matter of the present disclosure supports and provides sufficient basis for any element, feature, structure, function, and/or step of any aspect, and/or example embodiment described in the present disclosure including the figures, clauses and/or claims herein to be claimed alone in an independent claim and be fully supported herein, or be combined with any other one or more elements, features, structures, functions, and/or steps of any aspect and/or example embodiment described in the present disclosure including the figures, clauses and/or claims herein, as basis for an independent or dependent claim herein. With respect to the above description, it is to be realized that the dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

While the present disclosure describes various example embodiments, the disclosure is not so limited. To the contrary, the disclosure is intended to cover various modifications and equivalent arrangements, as will be readily appreciated by the person of ordinary skill in the art.

The invention claimed is:

1. A device for generating milling measurement data at an output, comprising:
   a support structure;
   a measurement station supported by the support structure for measuring an attribute of milled material collected thereon and outputting a measurement of the attribute to the output; and
   a mill supported by the support structure above the measurement station for performing a milling action on a feed material, and
   depositing milled material onto the measurement station wherein the measurement station can measure the milled material without interrupting the milling action,
   wherein the mill comprises a processing chamber for holding the feed material while it performs the milling action thereon.

2. A device as defined in claim 1, wherein the mill is configured to continuously, regularly, irregularly or intermittently perform the milling action.

3. A device as defined in claim 1, wherein the mill is configured to continuously, regularly, irregularly or intermittently deposit the milled material onto the measurement station.

4. A device as defined in claim 1, wherein the measurement station is configured to continuously, regularly, irregularly or intermittently measure the attribute.

5. A device as defined in claim 1, wherein the attribute is a weight of the milled material collected on the measurement station.

6. A device as defined in claim 5, wherein the measurement station comprises a weighing structure to weigh the milled material collected thereon.

7. A device as defined in claim 1, wherein the measurement station is configured to continuously, regularly, irregularly or intermittently output a measurement of the attribute.

8. A device as defined in claim 1, wherein the output is selected from at least one of a display or an input to a computer system.

9. A device as defined in claim 1, wherein the processing chamber comprises a plurality of test milling balls.

10. A device as defined in claim 1, wherein the processing chamber comprises an inlet aperture for accepting the feed material.

11. A device as defined in claim 10, wherein the processing chamber comprises an outlet aperture for depositing the milled material onto the measurement station.

12. A device as defined in claim 11, wherein the mill is movable between a loading position in which the mill is configured to accept introduction of the feed material therein through the inlet aperture and an operative position in which the mill is configured to continuously mill the feed material introduced while in the loading position and output the milled material through the outlet aperture onto the measurement station.

13. A device as defined in claim 12, further comprising a drive unit for rotating the processing chamber about a drive axis in the operative position.

14. A device as defined in claim 13, wherein the processing chamber is oriented while in the loading position such that the inlet aperture is oriented substantially upward and the processing chamber is oriented in the operative position such that the outlet aperture is oriented substantially downward.

15. A device as defined in claim 13, wherein the processing chamber is oriented while in the loading position such that the drive axis is inclined upward and in the operative position such that the drive axis is substantially horizontal.

16. A device as defined in claim 13, further comprising a controller in communication with the measurement station, the controller comprising, or configured to communicate with, a processor and a non-transient memory for storing instructions that, when executed by the processor, cause the controller to perform a test procedure, the test procedure comprising:

initiating the test procedure to measure the attribute of the milled material deposited on the measurement station and outputting the measurement of the milled material to the output; and terminating the test procedure when a condition is satisfied.

17. A device as defined in claim 16, wherein the controller is configured to enable the drive unit; and to terminate the test procedure by disabling the drive unit when the condition is satisfied.

18. A device as defined in claim 17, wherein the condition is satisfied by the measurement reaching a threshold value.

19. A device as defined in claim 18, wherein the threshold value is a proportion of an attribute of the feed material.

20. A device as defined in claim 1, wherein the processing chamber compromises an aperture for accepting the feed material and for depositing the milled material onto the measurement station.

21. A device as defined in claim 20, further comprising a mesh cover to cover the aperture, the mesh cover having openings of an opening size therein to deposit the milled material that is of a size less than the opening size onto the measurement station.

22. A device as defined in claim 21, wherein the mesh cover is removable.

23. A device as defined in claim 21, wherein the opening size corresponds to a designated mesh classification according to a designated test procedure.

24. A device as defined in claim 21, wherein the mesh cover is supported by a peripheral frame having a first mounting portion to engage a corresponding second mounting portion secured to the processing chamber.

25. A device as defined in claim 24, wherein the peripheral frame comprises a first flange portion and the processing chamber comprises a second flange portion wherein the first and second mounting portions comprise a releasable fastener for securing the first flange portion to the second flange portion.

* * * * *